United States Patent
Brownlee et al.

[11] Patent Number: 6,157,862
[45] Date of Patent: *Dec. 5, 2000

[54] SHAPED MULTIPLE ELECTRODE LEAD FOR IMPLANTABLE DEVICE

[76] Inventors: Robert R Brownlee, 229 E. Hubler Rd., State College, Pa. 16801; Jonathan Lee, 138 Spartina Ave., St Augustine, Fla. 32080

[*] Notice: This patent is subject to a terminal disclaimer.

[21] Appl. No.: 09/090,514

[22] Filed: Jun. 4, 1998

Related U.S. Application Data

[63] Continuation-in-part of application No. 08/625,067, Mar. 29, 1996, Pat. No. 5,772,693, which is a continuation-in-part of application No. 08/598,992, Feb. 9, 1996, abandoned.

[51] Int. Cl.[7] .................................................. A61N 1/05
[52] U.S. Cl. ............................................................ 607/123
[58] Field of Search .................................... 607/122, 123, 607/125

[56] References Cited

U.S. PATENT DOCUMENTS

| | | | |
|---|---|---|---|
| 5,482,037 | 1/1996 | Borghi | 607/125 |
| 5,628,779 | 5/1997 | Bornzin et al. | 607/123 |
| 5,772,693 | 6/1998 | Brownlee | 607/123 |

*Primary Examiner*—William E. Kamm
*Attorney, Agent, or Firm*—Beck & Tysver PLLC

[57] ABSTRACT

A single pass lead system for defibrillating the heart is shown. Portion of the lead is relatively stiff and holds the lead in the SVC. This stiff section extends into the atrium where good contact with the electrodes on the lead are maintained by the lead stiffness. A very flexible distal portion carries defibrillation leads into the ventricle.

7 Claims, 2 Drawing Sheets

Fig. 2

| | APPLICATION | CONFIG | VC COIL 36 | A-COIL 32 | V-COIL 28 | CAN 38 |
|---|---|---|---|---|---|---|
| HIGH ENERGY { 50 | V-DEFIB | A | x | | | x |
| | | B | x | | x | |
| | | C | | | x | x |
| | A-DEFIB | A | x | x | | |
| | | B | | x | x | |
| | | C | | x | | x |
| | TOTAL DEFIB | A | x | x | x | x |

| | APPLICATION | CONFIG | V-TIP 24 | V-RING 26 | V-COIL 28 | CAN 38 | ATRAIL 30 | ATRAIL 34 | A-COIL 32 | SVC 36 |
|---|---|---|---|---|---|---|---|---|---|---|
| LOW ENERGY { 52 | V-SENSE/PACE | A | x | x | | | | | | |
| | | B | x | | x | | | | | |
| | | C | x | | | x | | | | |
| | | D | x | | | | | | | x |
| | A-SENSE/PACE | E | | | | | x | | | |
| | | F | | | | | x | x | | |
| | | G | | | | x | | x | | |
| | | H | | | | x | x | x | | |
| | | I | | | | x | x | x | | |
| | | J | | | | | | | | x |
| | | K | | | | | x | x | x | |
| | | L | | | | | x | | x | x |
| | | M | x | | | | | x | | x |
| | | N | x | | | | | x | | |

SHAPED MULTIPLE ELECTRODE LEAD FOR IMPLANTABLE DEVICE

CROSS REFERENCE TO RELATED APPLICATIONS

The present application is a continuation in part of applicant's copending U.S. patent application Ser. No. 08/625,067 filed Mar. 29, 1996 now U.S. Pat. No. 5,772,693, which is in turn a continuation in part of U.S. patent application Ser. No. 08/598,992 filed Feb. 9, 1996, now abandoned. Each of these applications are incorporated by reference in their entirety.

FIELD OF THE INVENTION

The present invention relates generally to catheters or leads used with implantable generators such as cardiac defibrillators and pacemakers, and more particularly to a single pass lead with multiple electrodes for pacing and/or defibrillating the heart.

BACKGROUND OF THE INVENTION

Modem implantable cardiac generators such as cardioverters, defibrillators or pacers supply an electrical therapy to the heart. Many implantable cardioverter defibrillators deliver a tired therapy for the treatment of tachyarrhythmia and biphasic pulses for the treatment of fibrillation. That is the device operates in a conventional pacing modality for brady arrhythmia providing micro Joules of energy. Tachy arrhythmia may be treated automatically by the delivery of synchronized low energy pulses, while bouts of fibrillation may be treated with several Joules of energy. Given the wide range of energies delivered it has been difficult to design lead systems offering good performance for each of these therapies and there is a continuing need to improve lead design.

BRIEF DESCRIPTION OF THE DRAWINGS

Throughout the figures like reference numeral reefer to identical structure wherein:

FIG. 2 shows a table setting forth electrode combinations.

DETAILED DESCRIPTION

Figure 1:
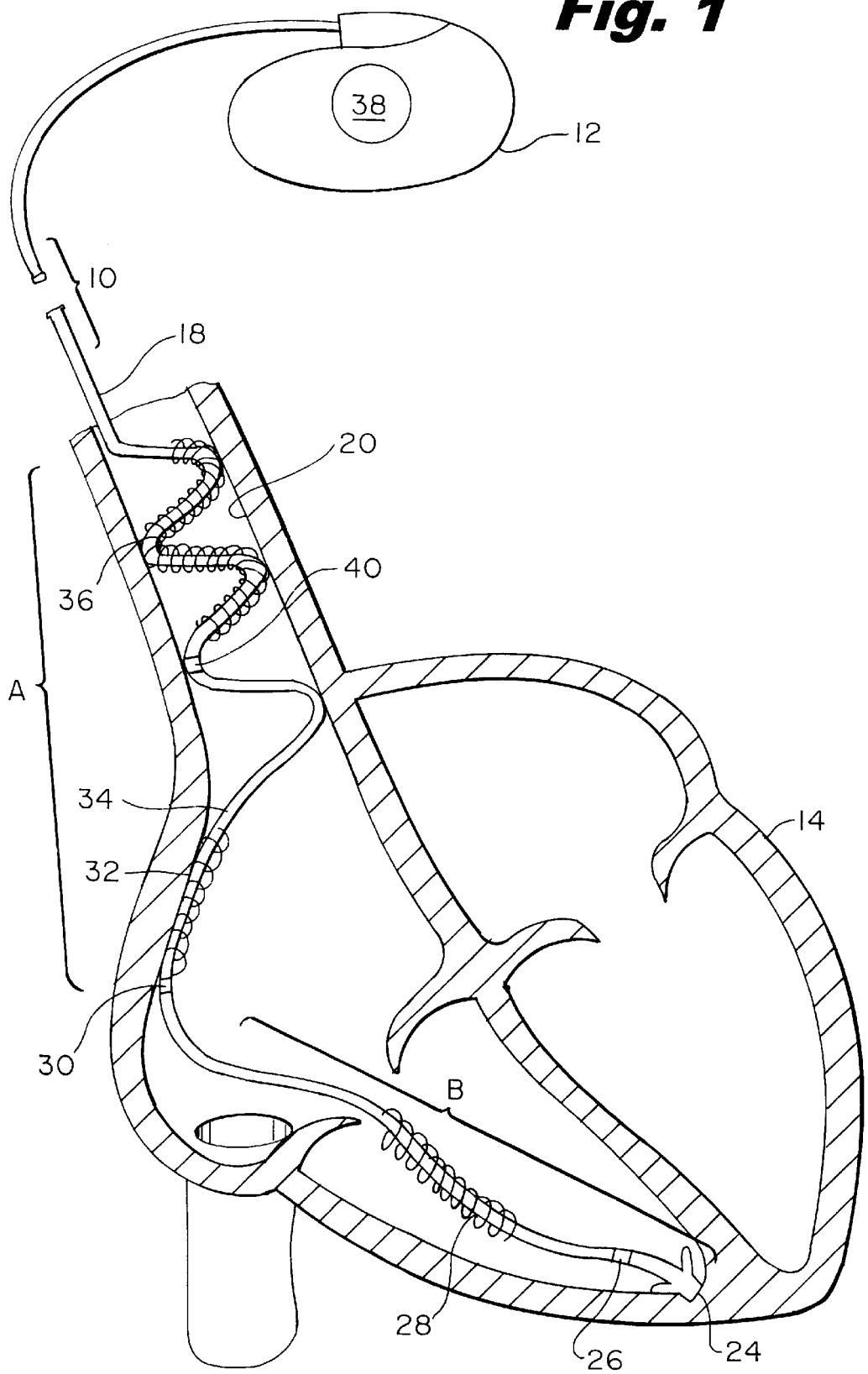
FIG. 1 shows a representative lead in a heart.

The lead system is described in the context of a permanent lead intended for insertion into the heart and used with use with an implantable pacer for control of arrhythmia or a cardioverter/defibrillator (ICD) of the type used for providing multiple energy level outputs in response to detected arrhythmia. Either of these devices may be referred to as a generator. The various lead locations presented on the illustrative example of the lead may be supplemented with additional structures and for certain applications one or more electrodes may be deleted from the lead structure. It should also be apparent that the lead may be used on a acute basis and removed after a period of time.

Turning to FIG. 1 the lead 10 is coupled to an implanted generator 12 and the distal end 18 of the lead is positioned in the heart 14. As more fully described in the incorporated references, the distal end 18 of the lead has two portions of unequal stiffness. A first portion is labeled alphabetically in the figures "A". Portion A positions the lead in or near the superior vena cava (SVC) 20 which is considered to be outside the heart. In its relaxed state this portion "A" of the lead occupies more length or volume than when it is inserted into the SVC. In general this portion of the lead will have a preformed serpentine shape when in its relaxed state when viewed in a plane. This portion of the lead may also be helical or spiral in shape. Therefore insertion in the SVC compresses the lead and in this stored energy state the lead portion A anchors the lead system into the beating heart. In chronic applications, the fibrotic response to the electrodes and lead structures causes the lead to be fibrosed and securely anchored in or close to the SVC. Lead portion A is relatively stiff and it acts as a cantilever support structure for the portion of the lead lodged in the atrium. After implantation this segment of the lead will also fibroses into place. Lead portion B is distal the portion A and it is relatively less stiff than portion A. It is intended that only the distal tip electrode 24 of portion B will fibroses into the apex of the ventricle. The length and physical characteristics of the portion B of the lead decouples the mechanical action of the ventricle from the atrium. It should be noted that all the atrial electrodes are carried on the portion "A" of the lead. Further details concerning the construction of the lead may be discerned from the companion application incorporated by reference. Although it is difficult to provide meaningful measurements of stiffness. The "stiff" portion A of the lead has the mechanical properties of a conventional pacing lead and portion B is relatively less stiff. In practice it may not be appropriate to have a distinct demarcation in stiffness between the two portions and the transition region may have variable stiffness to avoid stress in the lead. It should also be noted that the lead may be inserted with a stylet that both straightens and stiffen the led during implantation.

FIG. 1 also shows various electrodes which may be incorporated into the lead. In general the design places a coil electrode 36 outside the heart in the SVC but in contact with tissue The design also places a coil electrode 32 in the atrium and in contact with the atrium and the design places a coil electrode in the ventricle which does not contact the ventricle.

A conventional tip electrode 24 may be placed at the distal tip of the lead. A proximal ventricular ring electrode 26 may be placed "behind" or proximal the tip electrode 24. A "bump" electrode or convention ring electrode may be placed in portion B to contact the atria wall. A flexible large area "coil" electrode 32 may be placed on portion B to contact the atrium as well. Another more proximal bump electrode 34 may also contact the atrial wall. An SVC electrode 40 of conventional ring design may be provided in the SVC. The most proximal electrode may be a coil 36 located in the SVC. As is typical practice in this technology the can of the generator 12 may form an electrode 38 as well. It should be apparent that not all electrodes are required in any given design and various subsets of these electrode configurations are within the scope of the invention.

FIG. 2. is in the form of a table listing electrode configurations and combinations useful for low energy and high energy therapies. In general the useful pacing therapies and defibrillation waveforms are well known in this art and a full explanation of the pacing and defibrillation procedures need not need not be given in detail. However for the purposes of this disclosure it should be noted that biphasic therapy can be administered through the coils and that the presence of three coils permits achieving biphasic stimulation by holding one coil electrode t a reference voltage level and applying capacitor discharge between the other coils. FIG. 2 can be considered as divided into high energy configurations labeled 50 and low energy configurations 52. The table in the figure shows several possibilities for high energy therapy. It should be appreciated that the availability of several electrode wires at the generator allows multiphasic as well as monophasic waveforms with differing reference potentials. It should also be noted that both simultaneous use of multiple electrode s or sequential delivery are suitable. For example configuration "A" corresponds to the delivery of a shock from the SVC coil 36 to the ventricular coil 28. This configuration places much of the myocardium in the current path. Configuration "B" corresponds to the delivery of energy between three separate electrodes. Energy delivery between the SVC coil 36 and the atrial coil 28 or the can 38. Configuration C is the preferred arrangement for ventricular defibrillation with the energy delivered between the atrial coil 32 and the can 38 and between the ventricular coil 28 and the can 38. With regard to atrial defibrillation configurations A and C are equally preferred with energy delivery between the atrial coil 32 and either the SVC electrode 36 or can electrode 38 being useful. The "total" defibrillation configuration maximizes total lead surface area which may be desirable for the delivery of some energy levels. The low energy portion of the table sets forth various combinations of pacing and sensing electrode pairing. In general and in contrast to the defibrillation configurations only two electrodes are active during sensing or pacing. For delivery of pacing energy it is generally desirable to have small area electrodes. Sensing requirements are more difficult to quantify the area of the electrode is important but noise immunity may make some electrode combinations more suitable than others for a particular patient or class of patients.

Depending on the therapy suite administered by the generator some but not all of the lectrodes shown in the figure are necessary. To minimize complexity it may be desirable to share optimal defibrillation electrodes with a the pacing or sensing function resulting in usable but suboptimal pacing performance.

What is claimed is:

1. A lead for use in a patient, said lead having
   a lead body with a proximal end and a distal end, and having electrical conductor extending from said distal end to said proximal end, said proximal end having connectors coupled to each of said conductors, said distal end including;
   a first portion;
   a second portion;
   said first portion being connected to said second portion, and said first portion being relatively more stiff than said second portion;
   said first portion adapted for insertion into the superior vena cava of a patient and having a preformed shape which engages said superior vena cava and is elasticity deformed by said superior vena cava whereby it is retained in said superior vena cava;
   a first electrode located on said first portion;
   said first portion extending into said atrium wherein said first portion positions said electrode on said atrial portion in contact with said atrial wall, said atrial portion supported by its connection to said superior vena cava portion;
   a second electrode;
   said second portion relatively less stiff than said first portion for insertion into the ventricle to position said second electrode in said ventricular chamber.

2. The lead of claim 1 further including:
   a coil electrode located on said first portion whereby said coil electrode is positioned in the atrium of said patient.

3. The lead of claim 1 further including:
   a coil electrode located on said second portion whereby said coil electrode is positioned in the ventricle said patient.

4. The lead of claim 1 further including:
   a second coil electrode located on said first portion whereby said coil electrode is positioned in the atrium of said patient and a third coil electrode located on said second portion whereby said third electrode is positioned in said ventricle of said patient.

5. The lead of claim 1 further including:
   a small area electrode located on said first portion whereby said electrode is placed in said SVC of said patient.

6. The lead of claim 1 further including:
   a small area electrode located on said first portion whereby said electrode is positioned in said atrium of said patient.

7. The lead of claim 1 further including:
   a small area electrode located on said second portion whereby said electrode is placed in the ventricle of said patient.

* * * * *